United States Patent [19]

Hirata et al.

[11] Patent Number: 4,562,261

[45] Date of Patent: Dec. 31, 1985

[54] 2-GUANIDINOTHIAZOLINE COMPOUNDS, AND PROCESS FOR PREPARING THEM

[75] Inventors: Yasufumi Hirata, Saitama; Isao Yanagisawa, Tokyo, both of Japan

[73] Assignee: Yamanouchi Pharmaceutical Co., Ltd., Tokyo, Japan

[21] Appl. No.: 597,234

[22] Filed: Apr. 5, 1984

[30] Foreign Application Priority Data

Jun. 7, 1983 [JP] Japan .................................. 58-102206

[51] Int. Cl.$^4$ ............................................. C07D 277/18
[52] U.S. Cl. ..................................... 548/184; 548/193
[58] Field of Search .......................................... 548/184

[56] References Cited

U.S. PATENT DOCUMENTS 4,061,647 12/1977 Lang ................................... 548/184

Primary Examiner—Robert Gerstl
Attorney, Agent, or Firm—Burgess, Ryan & Wayne

[57] ABSTRACT

Novel 2-guanidinothiazoline compounds of the general formula

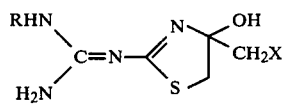

wherein R represents a hydrogen atom or a lower alkyl group, and X represents a halogen atom, and the acid addition salts thereof; they are important intermediate compounds for preparing famotidine and thiotidine which are medicaments useful as gastric acid secretion inhibitors.

4 Claims, No Drawings

2-GUANIDINOTHIAZOLINE COMPOUNDS, AND PROCESS FOR PREPARING THEM

DETAILED EXPLANATION OF THE INVENTION

The present invention relates to novel 2-guanidinothiazoline compounds, the acid addition salts thereof and the process for preparing them.

Thus, according to this invention, there are provided novel 2-guanidinothiazoline compounds of the general formula

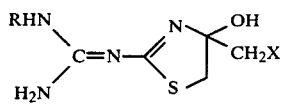

wherein R represents a hydrogen atom or a lower alkyl group, and X represents a halogen atom.

Furthermore, according to other embodiments of this invention, there is provided a process for preparing the novel 2-guanidinothiazoline compounds of the general formula I.

The term "lower" in the above definition means a straight or branched carbon chain having 1-5 carbon atoms. Suitable lower alkyl groups include a methyl group, an ethyl group, an isopropyl group, a butyl group, etc. Further, as the halogen atoms, there are a chlorine atom, bromine atom, iodine atom, etc.

Furthermore, the compounds of the general formula I can form acid addition salts thereof and there also exist the tautomers thereof. Therefore, the invention includes also the acid addition salts and the tautomers thereof.

As the acid addition salts, there are the salts of the compounds, with inorganic acids such as hydrochloric acid, hydrobromic acid, sulfuric acid, etc., and with aliphatic carboxylic acids, for example, acetic acid, maleic acid, fumaric acid, etc.

The compounds of the general formula I and the acid addition salts thereof provided by this invention are important intermediate compounds useful for preparing famotidine (cf. unexamined Japanese patent application laid open under the laying-open No. Sho.56-22770 and No. Sho.56-55383) and thiotidine (cf. unexamined Japanese patent application laid open under the laying-open No. Sho.53-147069) which are useful compounds for medical purposes as histamine H-2 receptor blockers or gastric acid secretion inhibitors.

Hitherto, as the intermediate compound for preparing such compounds, 2-guanidino-4-chloromethyl-thiazole (hereinafter referred to as "Compound A") is known from unexamined Japanese patent application laid-open under the laying-open No. Sho53-147069. However, Compound A is undesirable in that handling of the same is complicated since it has unfavorable properties such as an irritative odor, and causes contact dermatitis.

When the compounds of this invention shown by general formula I are used as intermediate compounds for preparing famotidine or thiotidine, the above problem connected with Compound A (that is, the problem of complicated handling) is avoided. In addition, the compounds of general formula I have the advantage that they can be obtained in high yield and are easy to purify. Thus, the compounds of this invention are useful intermediate compounds and can be advantageously used instead of Compound A.

The compounds of this invention shown by the general formula I can be produced by the following process.

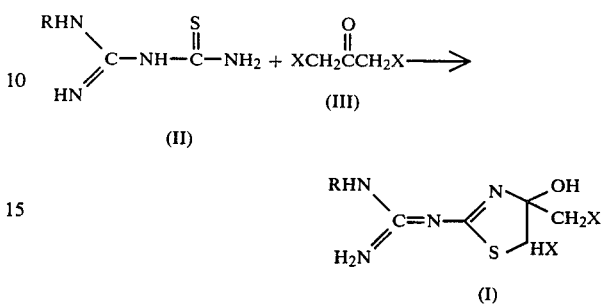

This process is performed by reacting the starting material compound of formula II and a reactive amount of the 1,3-dihalogenoacetone of formula III in an organic solvent under cooling. Any anhydrous organic solvents which are reaction inert, that is, which do not take part in the reaction may be used but acetone is preferably used. It is preferred that the reaction temperature is maintained between 0° C. and −10° C. In order to obtain the desired compound, the solid material formed in the reaction mixture is collected by filtration, and washed with water. The material thus obtained is pure enough to use for the next process as the intermediate material compound.

The following Examples will serve to illustrate the present invention, and the following Reference Examples will further serve to illustrate the preparation of famotidine in case of using the compounds of formula I. In the Examples and Reference Examples, m.p., Anal. and NMR are abbreviations for melting point, elementary analysis values and nuclear magnetic resonance spectrum, respectively. Example 1

N''-[4-(chloromethyl)-4,5-dihydro-4-hydroxy-2-thiazolyl]-guanidine hydrochloride 60.0 kg of dichloroacetone is dissolved in 550 ml of acetone. After cooling the solution to −5°∼−7° C., 55.8 kg of (aminoiminomethyl)thiourea [amidinothiourea] is added to the solution under cooling portionwise at one hour intervals each time in a 10 kg amount of amidinothiourea. The mixture is stirred continuously for 5 days below 0° C. The resultant precipitates are collected by filtration, and washed with 50 l of acetone to provide 111.6 kg of the desired compound. This material can be used as the starting material for the next process.

IR (KBr)$\nu_{max}$ 3200, 2880, 1680, 1595 cm$^{-1}$.

NMR (DMSO-d$_6$: 3.52 (AB$_q$, J=12 Hz, 2H, —S—C$\underline{H}_2$—); 3.80 (S, 2H, —C$\underline{H}_2$Cl); 6.96 (bs, 1H, —O$\underline{H}$); 8.04 (bs, 4H,

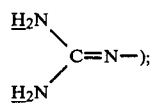

9.60 (bs, 1H, $\underline{H}$Cl).

REFERENCE EXAMPLE 1

N"-[4-[[(aminoiminomethyl)thio]methyl]-2-thiazolyl]-guanidine dihydrochloride

In 500 ml of water are dissolved 111.6 kg of the material obtained in Example 1 and 32.9 kg of thiourea. The solution is stirred for one hour at 50°~55° C. to complete the reaction.

(N'-[4-[[(aminoiminomethyl)thio]methyl]-2-thiazolyl]-guanidine dihydrochloride is formed in the reaction mixture, and this reaction mixture containing this compound is directly used for the next process without isolation of the formed compound)

REFERENCE EXAMPLE 2

N"-[4-[[(2-cyanoethyl)thio]methyl]-2-thiazolyl]-guanidine

The reaction mixture obtained in Reference Example 1 is cooled below 10° C., and to the solution are added 45.6 kg of -chloropropionitrile and 200 l of isopropanol. A solution of 69.1 kg of sodium hydroxide in 280 l of water is added dropwise to the solution under nitrogen stream followed by stirring for 2 hours at 0° C. 10° C. The crystals precipitated are collected by filtration, and washed with cold water and dried to provide 91.7 kg of the desired compound. m.p. 125–126.5 C.

REFERENCE EXAMPLE 3

Methyl 3-[[[2-[(diaminomethylene)amino]-4-thiazolyl]methyl]-thio]propionimidate

In 60 l of anhydrous dimethylformamide is dissolved 34.3 kg of the material formed in Reference Example 2. After adding 60 l of anhydrous methanol to the solution, 61.9 kg of hydrogen chloride gas is passed through the solution below 5° C. After stirring the reaction mixture for 2 days at 0° C.~5° C., the reaction mixture is poured into a mixture of 350 l of water, 250 kg of potassium carbonate, 30 l of ethyl acetate and ice while stirring below 5° C. the reaction mixture is stirred for 2 hours at 0° C.~5° C., and the resultant precipitates are collected by filtration. After stirring a mixture of the precipitates and 400 l of water for 0.5 hour at 0° C. 5° C., the resultant precipitates are collected by filtration, washed with 40 l of water and 10 l of cooled acetone respectively, and dried at reduced pressure to provide 30.6 kg of the desired product showing a melting point of 125.7° C.

REFERENCE EXAMPLE 4

3-[[[2-[(diaminomethylene)amino]-4-thiazolyl]methyl]-thio]-N-sulfamoylpropionamidine (generic name: famotidine)

In 340 l of methanol is dissolved 88.4 kg of sulfamide under heating, and the solution is cooled to 30° C. To the solution, 114.2 kg of the material obtained in Reference Example 3 are added portionwise three times while stirring at 20° 30° C. (The second addition is added 8 hours after the first addition, and the third addition is added 24 hours after the first addition.) After stirring the reaction mixture for a further 2 days at 20°~30° C., the crystals formed are collected by filtration, washed with 200 l of cooled methanol, and air-dried at room temperature to provide 87.5 kg of the desired product showing a melting point of 157.6° C. Some of the obtained product is recrystallized from dimethylformamide-water(:), and is dissolved in an equivalent molar amount of aqueous acetic acid (%). To the solution is added an equivalent molar amount of a dilute sodium hydroxide solution (%) in water to separate crystals showing the following physicochemical properties:

(I) m.p. 163~164 C.

(II) Anal. (for $C_8H_{15}N_7O_2S_3$):

|  | C (%) | H (%) | N (%) |
|---|---|---|---|
| Calculated: | 28.48 | 4.48 | 29.06 |
| Found: | 28.37 | 4.48 | 28.97 |

(III) NMR (DMSO-$d_6$): 2.50 (2H, m, —SCH$_2$CH$_2$—); 2.65 (2H, m, —SCH$_2$CH$_2$—); 3.60 (2H, s,

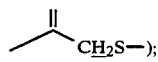

CH$_2$S—);

6.45 (1H, s,

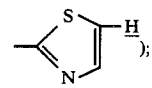

);

(IV) Mass. (FD method) m/e 338.

We claim:

1. 2-Guanidinothiazoline compounds of the general formula

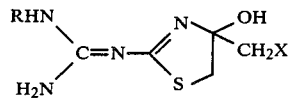

wherein R represents a hydrogen atom or a lower alkyl group, and X represents a halogen atom, and the acid addition salts thereof.

2. Compounds as claimed in claim 1, wherein said lower alkyl group contains from 1 to 5 carbon atoms.

3. Compounds as claimed in claim 1, wherein X is selected from the group consisting of chlorine, bromine, and iodine.

4. N"-[4-(chloromethyl)-4,5-dihydro-4-hydroxy-2-thiazoly]-guanidine.

* * * * *